(12) United States Patent
  Chen et al.

(10) Patent No.: US 12,682,607 B2
(45) Date of Patent: Jul. 14, 2026

(54) ULTRASOUND IMAGE DETECTION SYSTEM AND METHOD THEREOF BASED ON ARTIFICIAL INTELLIGENCE (AI) AUTOMATIC LABELING OF ANATOMICAL STRUCTURES

(71) Applicant: NATIONAL TAIWAN UNIVERSITY, Taipei City (TW)

(72) Inventors: Wen-Shiang Chen, Taipei City (TW); Chung-Ping Chen, Taipei City (TW); Hsin-Yuan Chu, Taipei City (TW)

(73) Assignee: NATIONAL TAIWAN UNIVERSITY, Taipei City (TW)

( * ) Notice: Subject to any disclaimer, the term of this patent is extended or adjusted under 35 U.S.C. 154(b) by 271 days.

(21) Appl. No.: 18/406,883

(22) Filed: Jan. 8, 2024

(65) Prior Publication Data

US 2024/0233330 A1     Jul. 11, 2024

Related U.S. Application Data

(60) Provisional application No. 63/479,150, filed on Jan. 9, 2023.

(30) Foreign Application Priority Data

Jul. 25, 2023    (TW) ................................. 112127761

(51) Int. Cl.
  *G06V 10/764*     (2022.01)
  *A61B 8/00*       (2006.01)
  (Continued)

(52) U.S. Cl.
  CPC ............ *G06V 10/764* (2022.01); *A61B 8/461* (2013.01); *A61B 8/469* (2013.01); *A61B 8/5223* (2013.01);
  (Continued)

(58) Field of Classification Search
  CPC ....................................................... G06V 10/82
  See application file for complete search history.

(56) References Cited

U.S. PATENT DOCUMENTS

2015/0238148 A1 *   8/2015   Georgescu .............. G06F 18/28
                                                            600/408
2019/0205606 A1 *   7/2019   Zhou ...................... G06N 3/045
                                (Continued)

*Primary Examiner* — Akwasi M Sarpong
*Assistant Examiner* — Michael L Burleson
(74) *Attorney, Agent, or Firm* — Studebaker Brackett PLLC

(57) ABSTRACT

Provided are an ultrasound image detection system and a method thereof based on artificial intelligence (AI) automatic labeling of anatomical structures, including: a receiving module, an image recognition module having an object detection model, an image processing module and a display module, wherein the image recognition module utilizes the object detection model to perform object detection on the image to be recognized, which is received by the receiving module, and then obtains a plurality of object recognition images with object detection results. Then, the image processing module detects missed anatomical structures according to the object detection results of the plurality of object recognition images, thereby outputting an object detection image. Additionally, the display module displays the object detection image. Therefore, the anatomical structures in the ultrasound image can be automatically and instantly recognized by AI so as to provide accurate judgment basis for medical personnel.

8 Claims, 17 Drawing Sheets

(51) Int. Cl.
    *G06V 10/77*        (2022.01)
    *G06V 10/774*      (2022.01)
    *G06V 10/776*      (2022.01)

(52) U.S. Cl.
    CPC ...... *G06V 10/7715* (2022.01); *G06V 10/7753*
            (2022.01); *G06V 10/776* (2022.01); *G06V*
                  *2201/033* (2022.01)

(56)         References Cited

U.S. PATENT DOCUMENTS

| | | | |
|---|---|---|---|
| 2019/0311205 A1* | 10/2019 | Mittal | G06F 18/214 |
| 2020/0034645 A1* | 1/2020 | Fan | G06V 10/25 |
| 2021/0077068 A1* | 3/2021 | Lu | G06V 10/764 |
| 2021/0150282 A1* | 5/2021 | Chadha | G06N 3/09 |
| 2021/0216822 A1* | 7/2021 | Paik | G10L 15/22 |
| 2022/0207718 A1* | 6/2022 | Wang | G06T 7/0012 |
| 2025/0104226 A1* | 3/2025 | Kolmer | G06V 10/82 |

\* cited by examiner

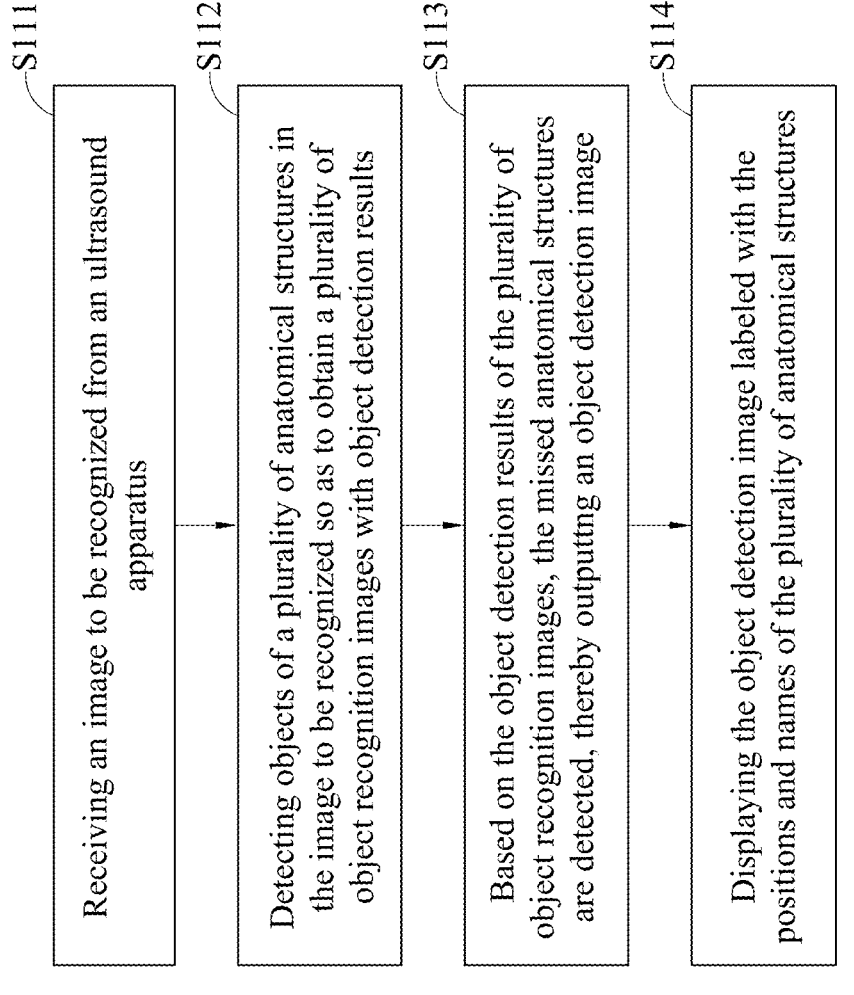

S111

Receiving an image to be recognized from an ultrasound apparatus

S112

Detecting objects of a plurality of anatomical structures in the image to be recognized so as to obtain a plurality of object recognition images with object detection results

S113

Based on the object detection results of the plurality of object recognition images, the missed anatomical structures are detected, thereby outputtng an object detection image

S114

Displaying the object detection image labeled with the positions and names of the plurality of anatomical structures

FIG. 11

ULTRASOUND IMAGE DETECTION SYSTEM AND METHOD THEREOF BASED ON ARTIFICIAL INTELLIGENCE (AI) AUTOMATIC LABELING OF ANATOMICAL STRUCTURES

CROSS-REFERENCE TO RELATED APPLICATION

The present disclosure claims the benefit of U.S. Provisional Patent Application No. 63/479,150, filed on Jan. 9, 2023, which is incorporated by reference herein in its entirety.

TECHNICAL FIELD

The present disclosure relates to a skeletal muscle recognition technology, and more particularly, to an ultrasound image detection system and method thereof based on artificial intelligence (AI) automatic labeling of an anatomical structure.

BACKGROUND

Modern people often have soft tissue lesions or pain in the musculoskeletal system. Causes of problems include aging, overuse, sports injuries, occupational injuries, etc. Although limb soreness or pain is not life-threatening, it can have a serious impact on life. Diseases of the musculoskeletal system are also the most common problems in rehabilitation clinics and orthopedic clinics.

Ultrasound examination has been applied to the examination of the musculoskeletal system for at least 15 years. Medical ultrasound has been one of the fastest-growing and most specialized technologies in recent years. For example, it can be used to diagnose tendon, ligament, muscle, nerve and joint diseases. In recent years, due to the improvement of ultrasound resolution and advancement of various software and computers, the diagnostic accuracy of ultrasound examination for superficial tissue has been continuously improved and confirmed. Ultrasound technology for soft tissues such as tendons, ligaments, muscles, joints, nerves and blood vessels is often called "skeletal muscle ultrasound" or "soft tissue ultrasound."

The advantages of using an ultrasound machine as an imaging inspection machine include: (1) no radiation exposure, so it is suitable for repeated use and tracking of patients; (2) cheaper (compared to magnetic resonance imaging [MRI]), in line with the principles of health care, suitable for screening patients; (3) non-invasive (compared to arthroscopy), easier to be accepted by patients; (4) dynamic examination being performed, having irreplaceable diagnostic value for certain lesions that only occur during movements, such as tendon adhesion and shoulder pinch symptoms; and (5) blood flow examination being performed without adding contrast agent and the amount of blood flow being an indispensable information for many diseases. In addition, the ultrasound scanner is a soft tissue imaging inspection tool that clinicians (such as from the rehabilitation department, orthopedic department, rheumatology department and immunology department, etc.) can operate by themselves. It can be used immediately in the outpatient clinic to determine the root cause of the patient's problem and treat it. Other imaging tools (e.g., X-ray, computed tomography scan, magnetic resonance imaging and arthroscopy) are not examinations that physicians can perform on their own in outpatient clinics.

In recent years, musculoskeletal ultrasound imaging examination is the most commonly used tool for diagnosing lesions or pain in the musculoskeletal system, and it can also be used for interventionally guided injections. However, ultrasound examination will have different interpretation results due to different machines, operator experience, knowledge and judgment. Musculoskeletal ultrasound faces many body parts with complex anatomical structures, and the three-dimensional relationship of nerves, muscles, tendons, blood vessels and other tissues in various parts is complex, and pathological tissues change in various ways. If ultrasound is not used frequently, it is difficult to grasp the images of all parts. Hence, there are issues in which body parts are difficult to be recognized. This makes many beginners face the dilemma of hard to find teachers and high learning threshold, and it is difficult to master ultrasound examination by using existing maps with limited images to learn by themselves.

As shown in FIG. 1A, which shows the axial musculoskeletal ultrasound image near the elbow joint, this is what's actually been seen during the examination. The complex anatomical structure can be seen. Specialists who do not routinely perform musculoskeletal ultrasound examinations have difficulty recognizing the names of the individual anatomical structures. Without knowing the appearance of the normal structure, it is inconceivable to make a correct imaging diagnosis in the case of abnormal tissues. As shown in FIG. 1B, it shows the ultrasound image of the axial skeletal muscles near the elbow joint labeled in textbooks, in which muscles, blood vessels and nerves are intermingled with considerable complexity. Further, FIG. 2A is an ultrasound image showing the longitudinal unlabeled elbow joint after a 90-degree rotation, and FIG. 2B is an ultrasound image showing the longitudinal labeled elbow joint after a 90-degree rotation. Similarly, although FIG. 2A is unlabeled and the ultrasound image is quite clear and beautiful, it is difficult for non-experts to recognize the names of the individual structures, thus causing a high threshold for the study of musculoskeletal ultrasound. It is difficult for general clinicians, especially primary care physicians who have to deal with the general public, to make correct diagnosis and treatment for the musculoskeletal system pain (e.g., shoulder pain, knee pain, low back pain, etc.) faced by patients. As such, even though ultrasound for diagnosis is quite common, and many clinics also purchase the ultrasound machine, the ultrasound examination cannot smoothly play a role in diagnosing pain in musculoskeletal joints.

Therefore, it has become an urgent issue to be solved in the art on how to quickly and correctly judge the three-dimensional relationship between nerves, muscles, tendons, blood vessels and other tissues in various parts of the ultrasound images of the skeletal muscles, thereby providing medical professionals with correct diagnosis and treatment.

SUMMARY

In order to solve the aforementioned prior art technical issues or provide related effects, the present disclosure provides an ultrasound image detection system based on artificial intelligence automatic labeling of an anatomical structure. The ultrasound image detection system comprises: a receiving module configured to receive an image to be recognized from an ultrasound apparatus; an image recognition module having an object detection model and communicatively connected to the receiving module to receive the image to be recognized, such that the object detection model is used to detect a plurality of anatomical structures in the image to be recognized, thereby obtaining a plurality of object recognition images with object detection results; an image processing module communicatively connected to the image recognition module to receive the plurality of object recognition images, such that a confidence index of anatomical structures in the plurality of object recognition images is computed according to the object detection results of the plurality of object recognition images so as to detect missed anatomical structures, thereby outputting an object detection image; and a display module communicatively connected to the image processing module to receive the object detection image and display the object detection image in real time.

The present disclosure further provides an ultrasound image detection method based on artificial intelligence automatic labeling of an anatomical structure, the ultrasound image detection method comprises: receiving an image to be recognized from an ultrasound apparatus by a receiving module; receiving the image to be recognized from the receiving module by an image recognition module having an object detection model, such that the image recognition module uses the object detection model to detect a plurality of anatomical structures in the image to be recognized, thereby obtaining a plurality of object recognition images with object detection results; receiving the plurality of object recognition images from the image recognition module by an image processing module, such that a confidence index of anatomical structures in the plurality of object recognition images is computed according to the object detection results of the plurality of object recognition images so as to detect missed anatomical structures, thereby outputting an object detection image; and receiving the object detection image by a display module to display the object detection image in real time.

In one embodiment, the present disclosure further comprises an automatic labeling module communicatively connected to the image recognition module and configured to use a semi-supervised learning to train a teacher model and a student model, such that the automatic labeling module uses the trained teacher model to label unlabeled plural ultrasound images to generate a plurality of training images, thereby providing for the image recognition module to train the object detection model.

In one embodiment, the image processing module uses at least one of the plurality of object recognition images received first as at least one reference image and the other one of the plurality of object recognition images received subsequently as an image to be recognized, such that a new confidence index of the plurality of anatomical structures in the image to be recognized is computed according to object detection results of the image to be recognized and the reference image so as to label missed anatomical structures in the image to be recognized, thereby detecting missed anatomical structures from the plurality of object recognition images.

In one embodiment, the object detection model includes a Focus framework which performs a slicing operation on the received image to be recognized, such that a feature map of the image to be recognized is obtained, thereby providing for the object detection model to detect a plurality of anatomical structures in the image to be recognized.

In one embodiment, the object detection image includes positions and names of the plurality of anatomical structures.

As can be seen from the above, the ultrasound image detection system and the method thereof based on artificial intelligence automatic labeling of an anatomical structure according to the present disclosure detect each of anatomical structures in an ultrasound image by an object detection model to label the position and name of each anatomical structure, obtain a plurality of object recognition images, and further compute a new confidence index of the anatomical structure by the object detection results of the plurality of object recognition images, so as to label the missed anatomical structures in the plurality of object recognition images, thereby increasing the accuracy of system inference and providing clear evidence for medical professionals to make correct diagnosis and treatment.

BRIEF DESCRIPTION OF THE DRAWINGS

FIG. 11 is a schematic flowchart showing an ultrasound image detection method based on AI automatic labeling of an anatomical structure according to the present disclosure.

DETAILED DESCRIPTION

The following describes the implementation of the present disclosure with examples. Those skilled in the art can easily understand other advantages and effects of the present disclosure from the contents disclosed in this specification.

It should be understood that, the structures, ratios, sizes, and the like in the accompanying figures are used for illustrative purposes to facilitate the perusal and comprehension of the contents disclosed in the present specification by one skilled in the art, rather than to limit the conditions for practicing the present disclosure. Any modification of the structures, alteration of the ratio relationships, or adjustment of the sizes without affecting the possible effects and achievable proposes should still be deemed as falling within the scope defined by the technical contents disclosed in the present specification. Meanwhile, terms such as "on," "above," "below," "first," "second," "a," "one" and the like are merely used for clear explanation rather than limiting the practicable scope of the present disclosure, and thus, alterations or adjustments of the relative relationships thereof without essentially altering the technical contents should still be considered in the practicable scope of the present disclosure.

Figure 3:
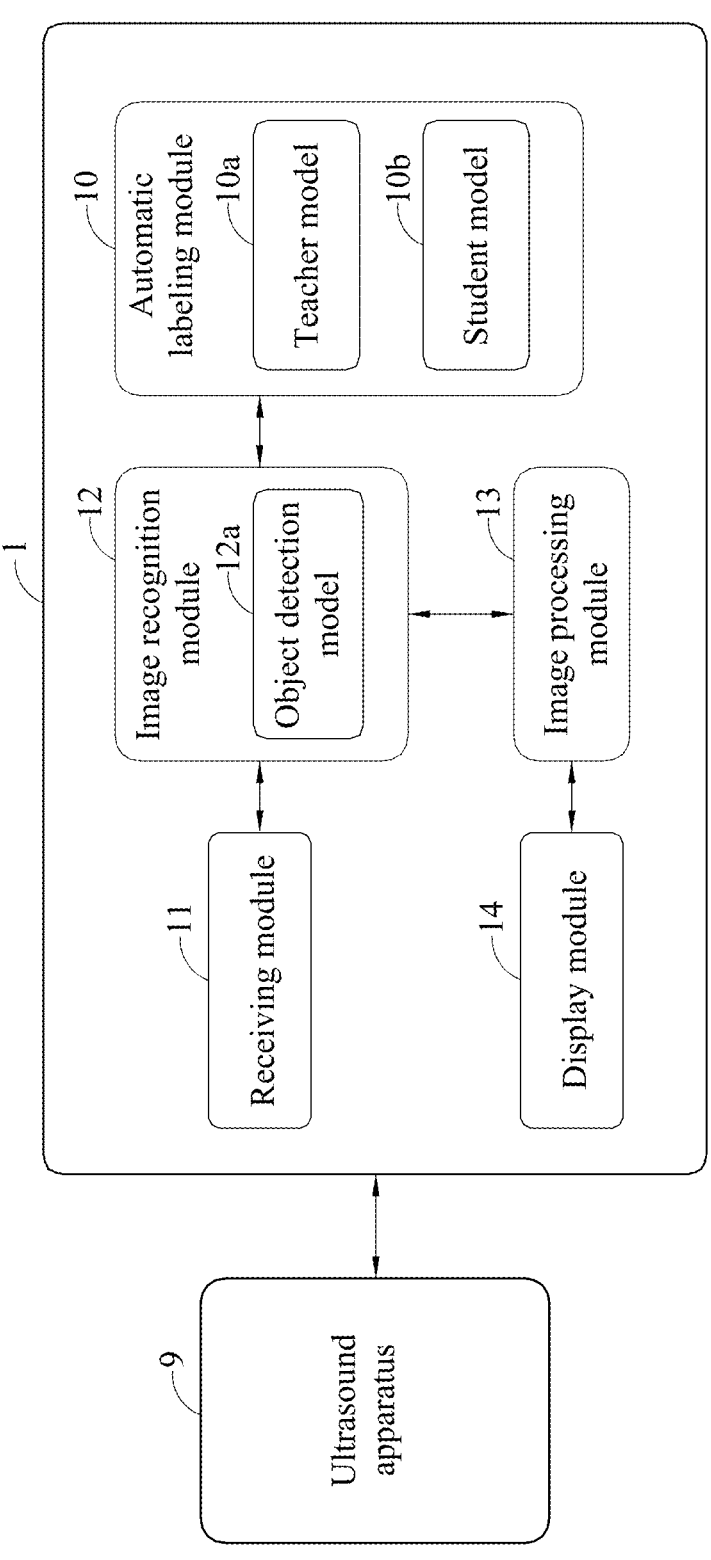
FIG. 3 is a schematic diagram showing a framework of an ultrasound image detection system based on artificial intelligence (AI) automatic labeling of an anatomical structure according to the present disclosure.

FIG. 3 is a schematic diagram showing a framework of an ultrasound image detection system 1 based on artificial intelligence (AI) automatic labeling of an anatomical structure according to the present disclosure. The ultrasound image detection system 1 is communicatively (or electrically) connected to an ultrasound apparatus 9 and includes an automatic labeling module 10, a receiving module 11, an image recognition module 12 having an object detection model 12a, an image processing module 13 and a display module 14.

Specifically, the ultrasound image detection system 1 based on AI automatic labeling of an anatomical structure can be established in electronic apparatuses with appropriate calculation mechanisms such as servers (e.g., general-purpose servers, file-type servers, storage unit-type servers, etc.) and computers, wherein each of the modules (namely the automatic labeling module 10, the receiving module 11, the image recognition module 12 having the object detection model 12a, the image processing module 13 and the display module 14) in the ultrasound image detection system 1 based on AI automatic labeling of an anatomical structure may be software, hardware, or firmware; if the modules are hardware, they may be processing units, processors, computers, or servers with data processing and computing capabilities; if the modules are software or firmware, they may include instructions executable by processing units, processors, computers, or servers, and may be installed on the same hardware device or distributed across a plurality of different hardware devices. In one embodiment, the ultrasound apparatus 9 may be an ultrasound scanner.

The receiving module 11 is communicatively (or electrically) connected to the ultrasound apparatus 9 so as to receive an image to be recognized from the ultrasound apparatus 9 (e.g., an ultrasound image of a film) or a plurality of training images (e.g., ultrasound images). In one embodiment, the receiving module 11 may also be communicatively (or electrically) connected to an electronic apparatus (e.g., a personal computer, a notebook computer) with an appropriate calculation mechanism to receive the plurality of training images.

The image recognition module 12 having the object detection model 12a is communicatively (or electrically) connected to the receiving module 11 to obtain the image to be recognized from the receiving module 11. In addition, objects of the plurality of anatomical structures (e.g., nerves, muscles, tendons, blood vessels, etc. in various parts) in the image to be recognized are detected by the object detection model 12a, and the positions and names of the plurality of anatomical structures in the image to be recognized are automatically labeled so as to obtain continuous plural object recognition images. Besides, the plural object recognition images include object detection results.

In one embodiment, the image to be recognized may be a video file, which includes a plurality of frames of images to be recognized. The plurality of anatomical structures in the plurality of frames of images to be recognized are detected by the image recognition module 12 via the object detection model 12a, so as to obtain the continuous plural object recognition images.

In one embodiment, the object detection results may be {[x1, x2, y1, y2, confidence, class]A, [x1, x2, y1, y2, confidence, class]B, . . . }, wherein x1, x2, y1 and y2 represent the bounding box coordinates of the detected objects A and B in the object recognition image; confidence represents the confidence index of the object detection model 12a on the objects A and B; and class represents which type of object (e.g., nerve, muscle, tendon, blood vessel, etc.) the objects A and B belong to.

In one embodiment, the image recognition module 12 further receives a plurality of training images from the ultrasound apparatus 9 or the electronic apparatus with an appropriate calculation mechanism, and the positions and names of the plurality of anatomical structures are labeled in the plurality of training images.

Specifically, the plurality of training images are collected by the image data collection stage, and the image data collection stage is as follows:

(1) Subject Selection Criteria
    (a) Inclusion conditions:
        Test group:
           (i) Normal people, taking upper limbs as an example, with no recent upper limb pain, i.e., Visual Analogue Scale (VAS) equal to 0 points, and one collection site includes forearm, elbow joint and upper arm.
           (ii) Over 20 years old, no upper age limit.
           (iii) The subject has signed the consent form before the test.
        Control group:
           (i) None.
    (b) Exclusion conditions: refusal to sign the subjects consent form.
(2) Test Design and Process
    (a) Collection of ultrasound images:
        (i) Image format: conventional grayscale ultrasound images (Toshiba, Philips, Hitachi).
        (ii) Collection time: outpatient clinic, ultrasound scan time about 20 minutes.
        (iii) Collection method: taking the upper limbs as an example (but not limited to the upper limbs), from the upper arm through the elbow joint to the wrist, three or so ultrasound grayscale images will be scanned, and the obtained ultrasound images of the skeletal muscles will be stored as training images.
(3) Test Period and Progress
    (a) Number of trial cases admitted:
        (i) Test group: 50 persons
        (ii) Control group: none
    (b) Test start time: from the test date, a period of one year.
(4) Image Data Processing
    (a) Organization and archiving of ultrasound images of skeletal muscles
    (b) Labeling: physician with more than three years of experience in ultrasound images of skeletal muscles (or soft tissues) anonymously labels names and positions of the plurality of anatomical structures collected on ultrasound images of skeletal muscles; the upper limbs are taken as an example (but not limited to the upper limbs), the positions and names of the labeled anatomical structures on the ultrasound image include but not limited to: Brachialis muscle, Brachiradialis muscle, Biceps brachi muscle, Pronator teres muscle, Supinator muscle, Flexor digitorum superficialis muscle, Flexor digitorum profundus muscle, Flexor policis longus muscle, Pronator quadratus muscle, Radial nerve, Ulnar nerve, median nerve, brachial artery, Brachial vein, Ulna bone, Radial bone, Humeral bone.

In one embodiment, the automatic labeling module 10 includes in the ultrasound image detection system 1 based on AI automatic labeling of an anatomical structure is communicatively (or electrically) connected to the image recognition module 12 to provide the plurality of training images, wherein the automatic labeling module 10 includes a teacher model 10*a* and a student model 10*b* based on a neural network (e.g., a convolution neural network), and the automatic labeling module 10 uses semi-supervised learning to train the teacher model 10*a* and the student model 10*b* to label the plurality of anatomical structures in the plurality of ultrasound images, thereby obtaining the trained teacher model 10*a*. As such, the plurality of anatomical structures in the ultrasound images are labeled by the trained teacher model 10*a* to obtain the plurality of training images.

Figure 4:
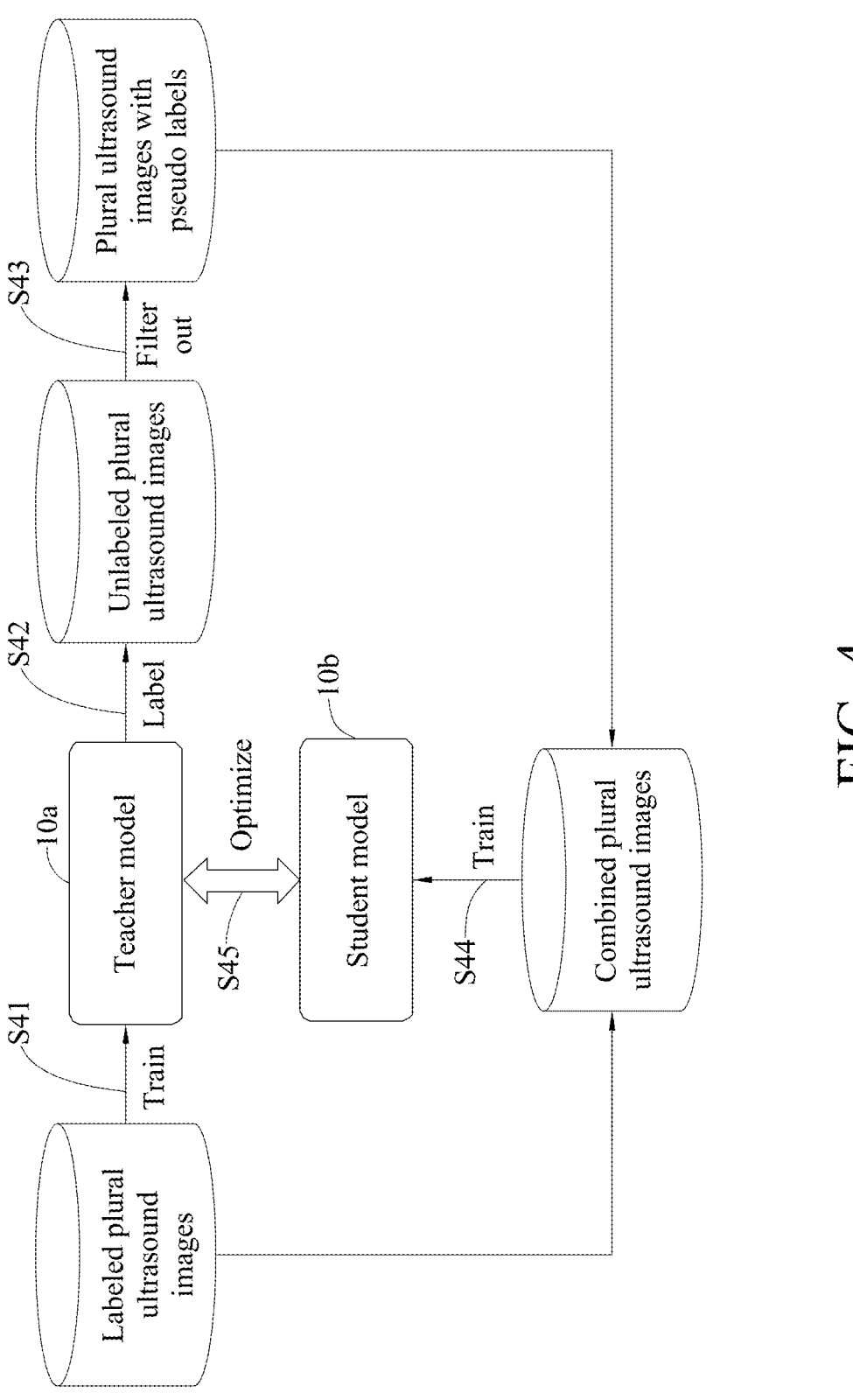
FIG. 4 is a schematic diagram showing a semi-supervised learning process according to the present disclosure.

Specifically, as shown in FIG. 4, the semi-supervised learning includes the following steps.

In step S41, the labeled plurality of ultrasound images are used as a training data set for deep learning to train a teacher model 10*a*. In one embodiment, the labeled plurality of ultrasound images are manually labeled.

In step S42, the teacher model 10*a* is used to label the unlabeled plurality of ultrasound images to obtain the plurality of ultrasound images with pseudo labels.

In step S43, the plurality of ultrasound images with pseudo labels generated by the teacher model 10*a* are filtered to filter out pseudo labels with poor quality. In one embodiment, the teacher model 10*a* is provided with a threshold. If the confidence index of a label recognized by the teacher model 10*a* is lower than the threshold, said label will be automatically filtered out.

In step S44, the plurality of ultrasound images with pseudo labels having better quality are added to the labeled plurality of ultrasound images to obtain the combined plurality of ultrasound images, and the combined plurality of ultrasound images are used as a new training data set, thereby using the new training data set to train a student model 10*b*.

In step S45, if the performance of the student model 10*b* is higher than that of the teacher model 10*a*, then the student model 10*b* is used as a new teacher model 10*a* for optimization, and returns to step S41 until the training is over, thereby obtaining the trained teacher model 10*a*.

In another embodiment, the image recognition module 12 establishes and trains the object detection model 12*a* by using a Convolutional Neural Network (CNN) in deep learning according to the plurality of training images. In other words, the object detection model 12*a* of the present disclosure is a You Only Look Once (YOLO) object detection model in the CNN so as to perform deep learning training on the object detection model 12*a* based on the plurality of training images, such that the trained object detection model 12*a* can recognize the positions and names of the plurality of anatomical structures from the image to be recognized, wherein the object detection model 12*a* includes the following two aspects.

Figure 5:
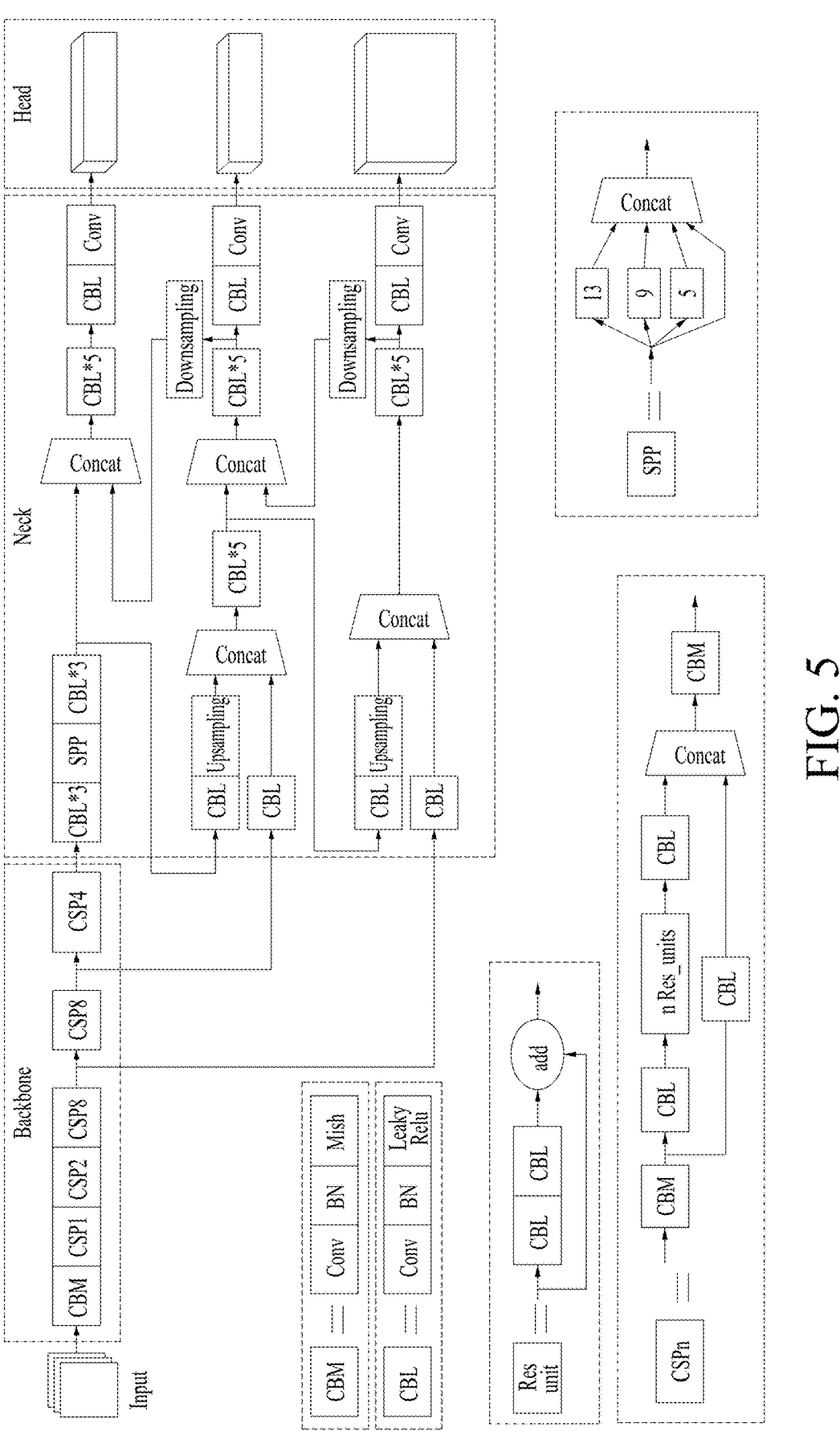
FIG. 5 is a schematic diagram showing a framework of an object detection model of YOLOv4.

In the first aspect, the object detection model 12*a* may be an object detection model based on YOLOv4, and as shown in FIG. 5, the framework of the object detection model 12*a* of YOLOv4 includes a Backbone, a Neck and a Head.

Figure 6:
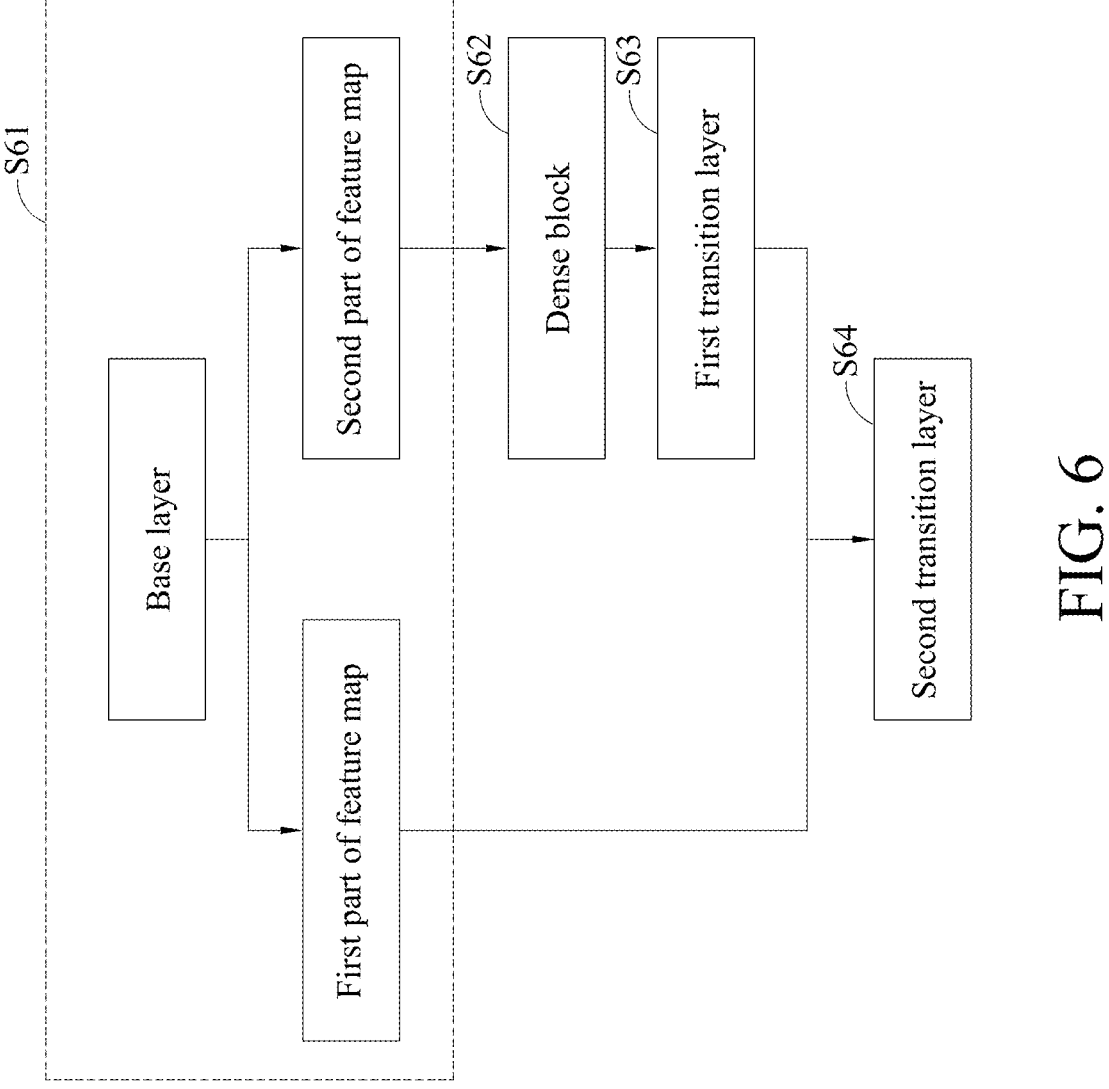
FIG. 6 is a schematic flowchart of CSPDarkNet53.

Specifically, the Backbone is CSPDarkNet53, such that the neural network framework can obtain richer gradient fusion information and reduce the amount of computation, wherein as shown in FIG. 6, the specific process of CSP-DarkNet53 includes the following steps.

In step S61, after CSPDarkNet53 inputs one of the plurality of training images, a feature map is obtained after the operations of convolution and pooling through the base layer, such that the feature map is used as the input of the neural network, and the feature map is divided into a first part and a second part.

In step S62, the second part of the feature map is convolved by a dense block and the number of channels is halved to obtain more feature information.

In step S63, the space size and the number of channels of the second part of the feature map are reduced by the first transition layer.

In step S64, after combining the first part of the feature map and the processed second part by the second transition layer, the space size and the number of channels of the reorganized feature map are also reduced to obtain a new feature map, wherein the new feature map contains low-level features and high-level features, which are conducive to improving accuracy of target detection.

In detail, through CSPDarkNet53, the object detection model 12*a* enables the present disclosure to achieve: (1) increasing the learning ability of the CNN and maintaining accuracy even if the model is lightweight; (2) removing the computing bottleneck structure with high computing power (reducing computing); and (3) reducing memory usage.

Moreover, the Neck is SPPnet+PANnet. Through the Neck, the receptive field is expanded and information of feature maps with different scales is fused (better feature fusion).

Figure 7A:
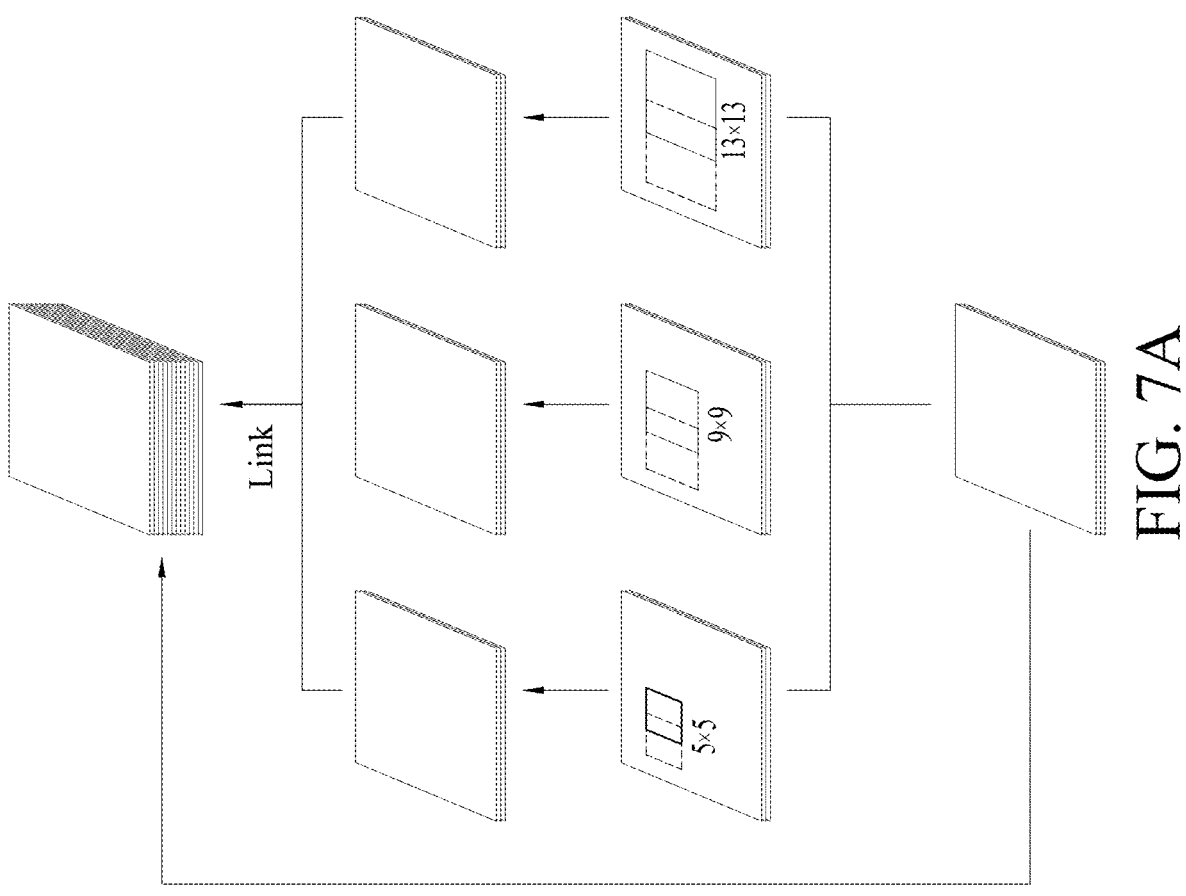
FIG. 7A is a schematic diagram showing a framework of SPPnet.

Specifically, as shown in FIG. 7A, the Spatial Pyramid Pooling (SPP) net is a pyramid network, which is connected to the spatial pyramid pooling layer after the last convolutional layer. The spatial pyramid pooling layer proposes a structure that maps and converts a feature with arbitrary size into feature vectors with fixed length, and then combines them into the following full connection layer whereby the input to a neural network may use images with arbitrary size to generate a fixed-size output. SPPNet extracts multi-layer features by spatial pyramid pooling to make target detection more accurate and faster and to improve the resilience of neural networks. Similarly, SPPNet combines global and sub-region information by maximum pooling layers with different sizes to extract feature vectors with different receptive fields. Accordingly, SPPNet has a better ability to describe detailed features and enhances accuracy of detecting different types of objects.

Figure 7B:
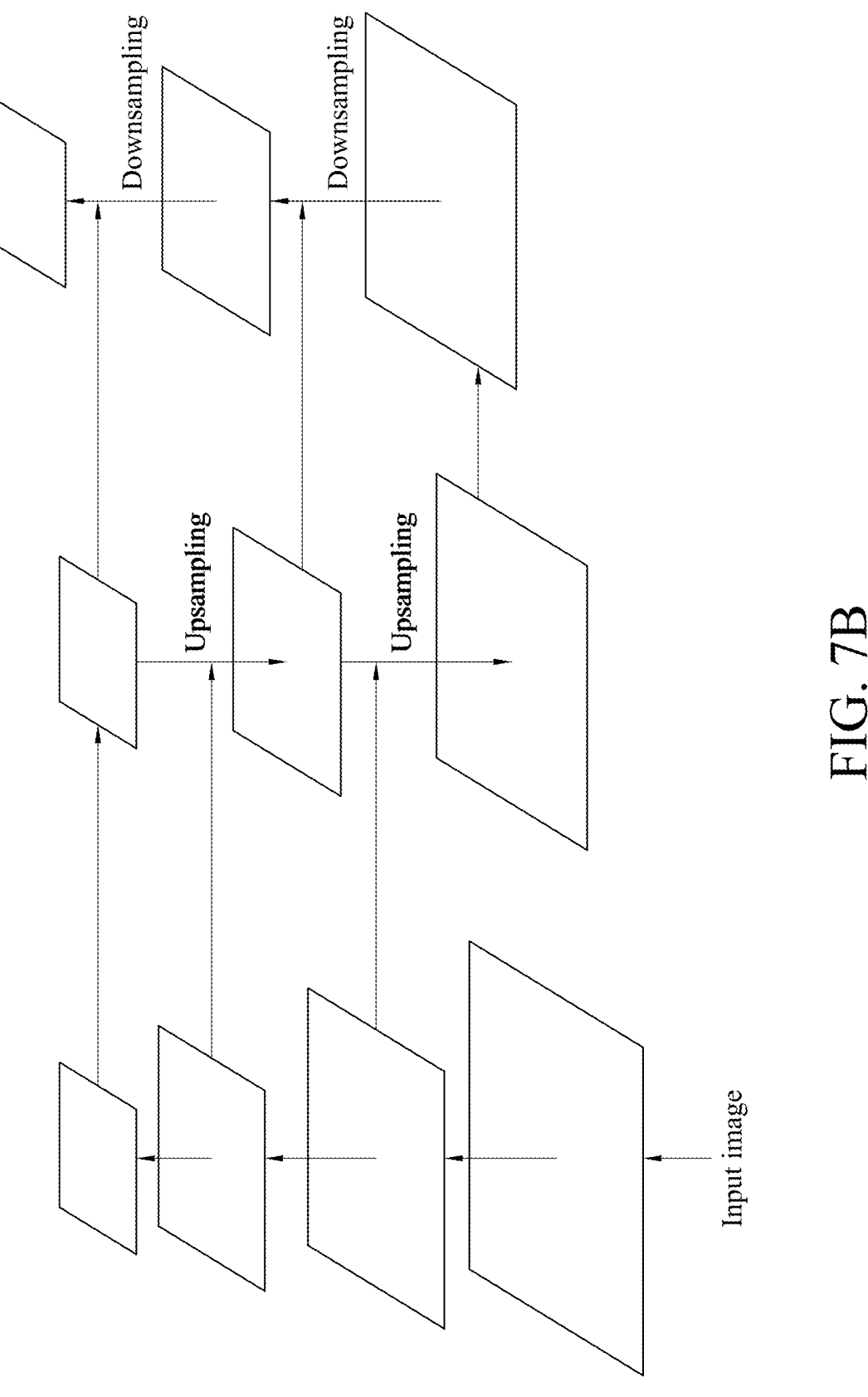
FIG. 7B is a schematic diagram showing a framework of PANet.

Further, in the backbone network, deep high-level features have more semantic meanings, while low-level information is more content descriptive. Therefore, using multi-layer features to make a discriminative/discerning pyramid network is very important for accuracy of object detection. As shown in FIG. 7B, Path Aggregation Network (PANet) improves the feature hierarchy based on Feature Pyramid Networks (FPN). The low-level information in deep layers is enhanced by an additional bottom-up path, and adaptive feature pooling is introduced to integrate features from all levels to improve predictive ability.

Figure 7C:
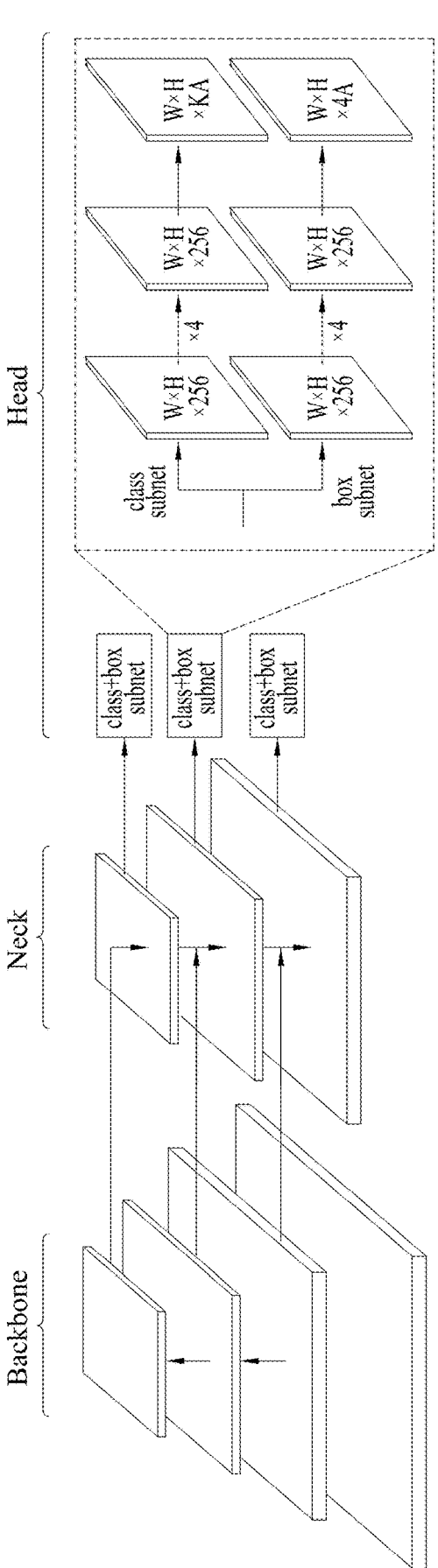
FIG. 7C is a schematic diagram showing three output heads.

Finally, Head is used for final detection, which applies anchor boxes on the feature map and produces a final output vector with class probabilities, object scores and bounding/encompassing boxes. As shown in FIG. 7C, there are three output heads, for example, the strides are 8, 16 and 32 respectively, such that the large output feature map detects small objects, and small output feature map detects large objects.

Figure 8:
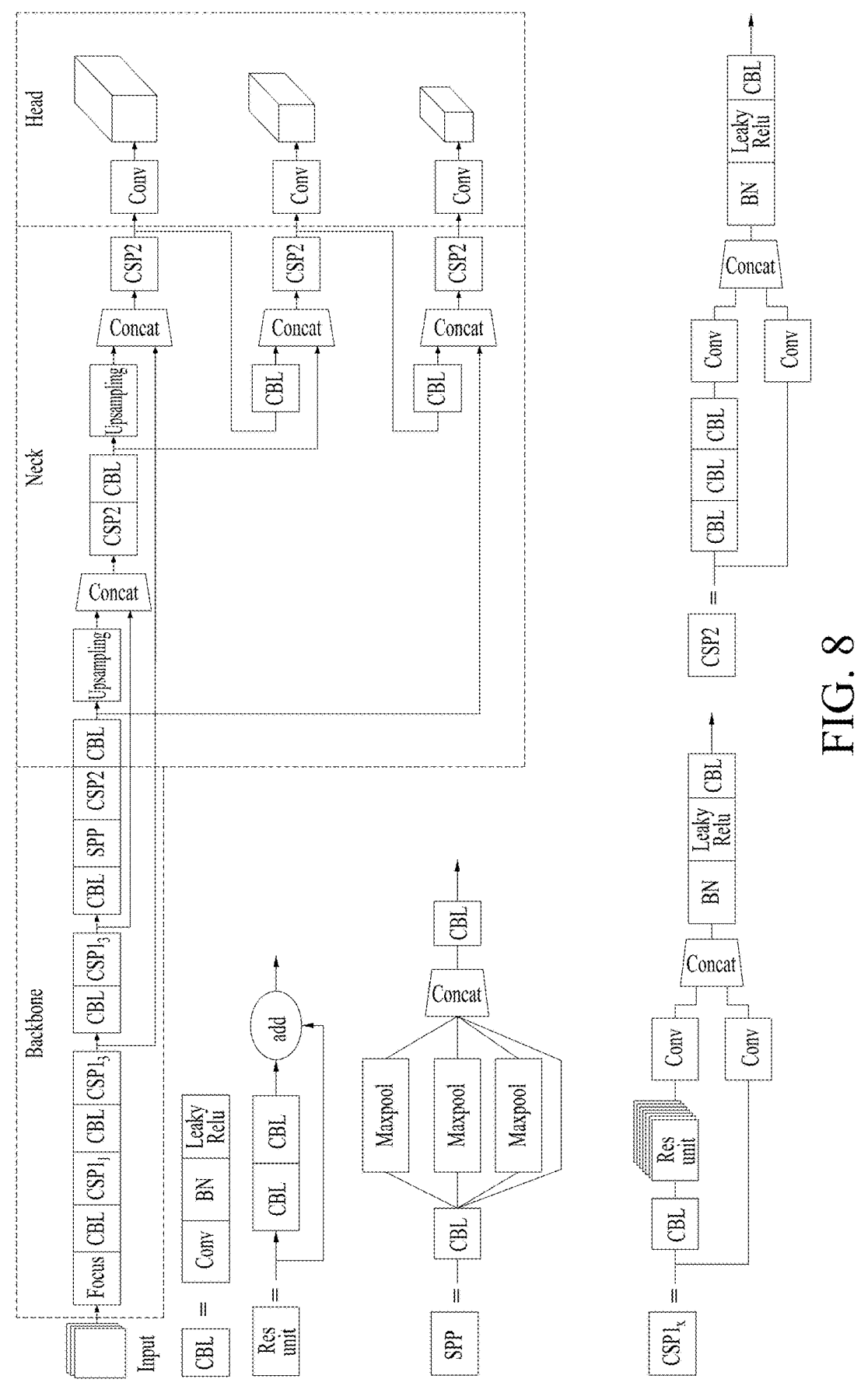
FIG. 8 is a schematic diagram showing a framework of an object detection model of YOLOv5.

In the second aspect, the object detection model 12*a* may be an object detection model based on YOLOv5, and as shown in FIG. 8, the framework of the object detection model 12*a* of YOLOv5 also includes a Backbone, a Neck and a Head. In addition, the parts of this aspect that are the same as those of the first aspect will not be repeated herein.

Figure 9A:
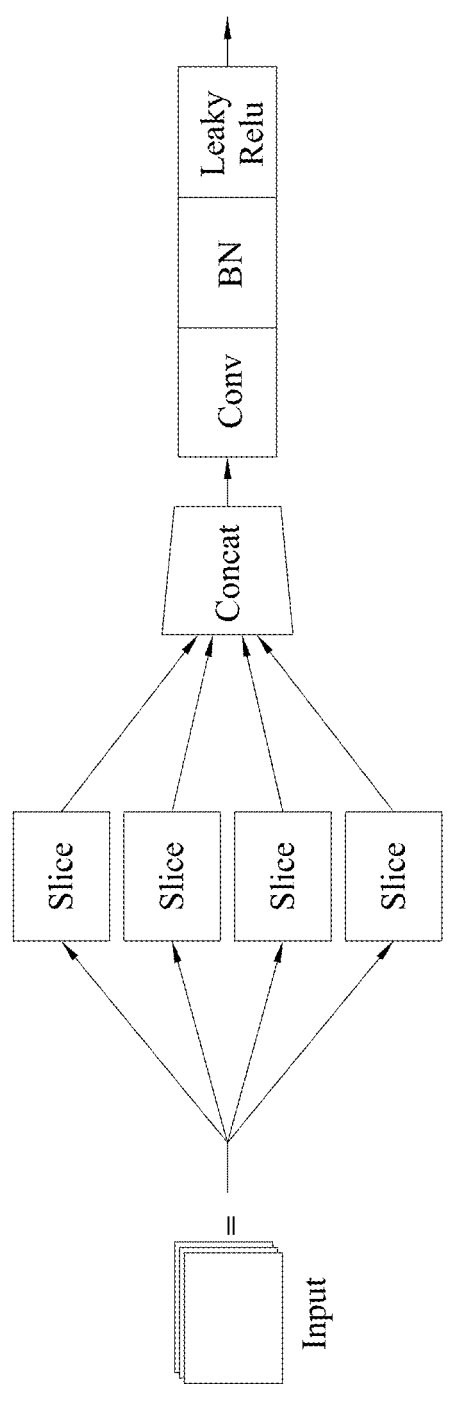
FIG. 9A is a schematic diagram showing a Focus framework.
Figure 9B:
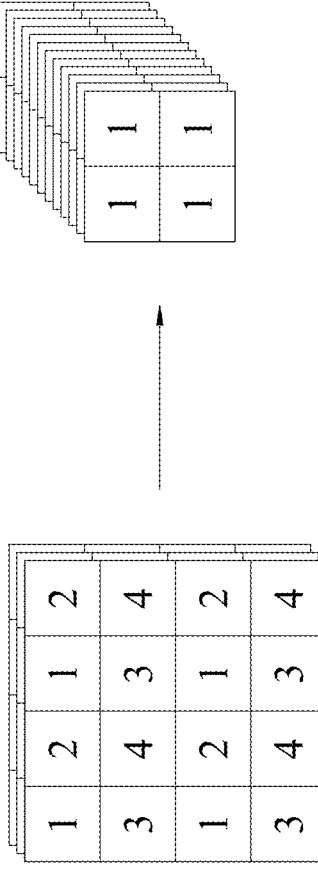
FIG. 9B is a schematic diagram showing a slicing operation of the Focus framework.

Specifically, as shown in FIG. 9A, the main difference between the second aspect and the first aspect is that the backbone of YOLOv5 in the second aspect further includes a Focus framework (also known as SpaceToDepth), and the Focus framework does not appear in YOLOv3 and YOLOv4. As shown in FIG. 9B, the Focus framework is used for slicing operations such that through the Focus framework, the original input image (e.g., the image to be recognized) is sliced into a feature map and then a convolution layer with 32 filters is applied, and final output is a feature map for the object detection model 12a to subsequently detect the plurality of anatomical structures in the image to be recognized. As such, the design of the Focus framework can reduce parameters of neural networks, reduce the size of the object detection model 12a and improve the operation speed.

The image processing module 13 is communicatively (or electrically) connected to the image recognition module 12 so as to sequentially receive the plurality of object recognition images from the image recognition module 12. In addition, the image processing module 13 uses at least one of the plurality of object recognition images received previously as at least one (e.g., one or a plurality of) reference image, and the other one of the plurality of object recognition images received subsequently is used as an image to be recognized. Then, the image processing module 13 computes a new confidence index of the plurality of anatomical structures in the image to be recognized based on the object detection result of the image to be recognized, the object detection result of the reference image and a decay coefficient so as to label the missed anatomical structures in the image to be recognized, thereby relabeling missed anatomical structures from the plurality of object recognition images so as to output an object detection image.

Figure 10:
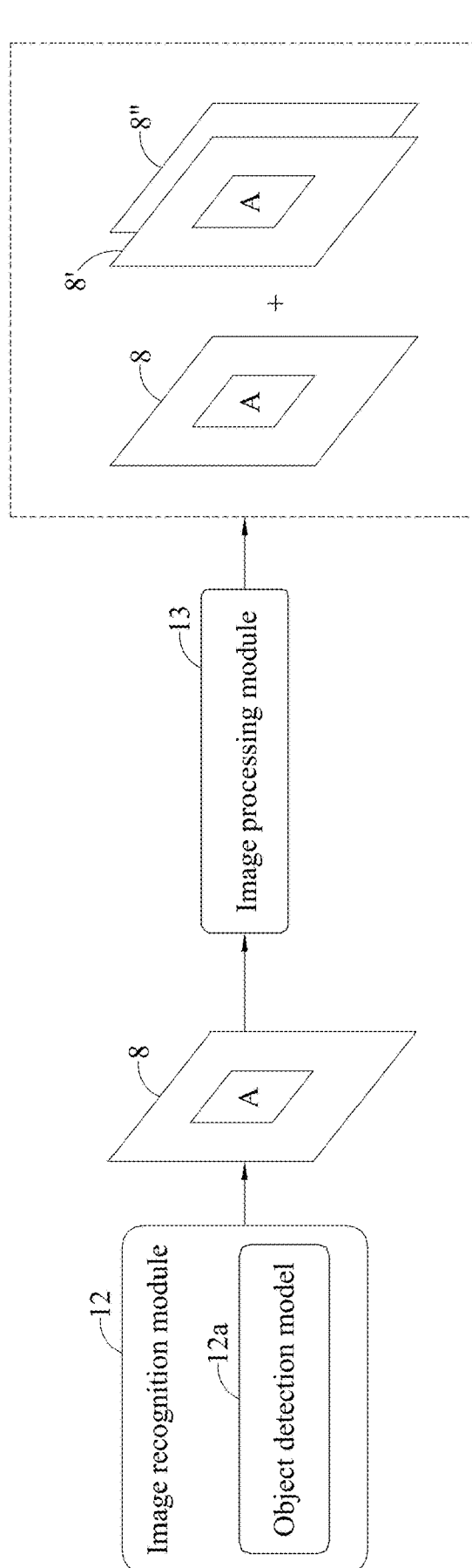
FIG. 10 is a schematic diagram of recognizing missed anatomical structures.

For example, as shown in FIG. 10, the image processing module 13 receives an object recognition image from the image recognition module 12 as an image 8 to be recognized, and the confidence index of the object A (i.e., the anatomical structure) in the object detection result of the image 8 to be recognized is 0.3. Additionally, the image processing module 13 uses two object recognition images received first as the first reference image 8' and the second reference image 8", and the confidence index of the object A in the object detection results of the first reference image 8' and the second reference image 8" is 0.5, wherein the image 8 to be recognized differs from the first reference image 8' by one image, so the distance is 1, and the image 8 to be recognized differs from the second reference image 8" by two images, so the distance is 2, whereby the image processing module 13 computes a new confidence index of the object A in the image 8 to be recognized according to formula (1).

$$C_j' = C_j + \sum_{i=1}^{n} \left( C_i \times \alpha^{D_{ij}} \right) \tag{1}$$

wherein i is the reference image; j is the image to be recognized;

$$C_j'$$

is the new confidence index of an object in the image to be recognized; $C_j$ is the original confidence index of an object in the image to be recognized; $C_i$ is the confidence index of an object in the reference image; $\alpha$ is the decay coefficient; and $D_{ij}$ is the distance between the reference image and the image to be recognized.

In this regard, the new confidence index $$\left( C_j' \right)$$

of the object A in the image 8 to be recognized is 0.3+(0.5×0.7)+(0.5×0.72)≅0.9, wherein the decay coefficient $\alpha$ is 0.7. It can be seen that when the original confidence index of the object A in the image 8 to be recognized is 0.3, the object A will be filtered out because its confidence index is too low, thereby causing misjudgment. However, the image processing module 13 refers to the confidence index of 0.5 of the first two reference images 8', 8" with the object A, such that the object A in the image 8 to be recognized can also be successfully recognized, thereby increasing the system inference accuracy; that is, the recognition accuracy of each anatomical structure in the plurality of object recognition images is improved.

The display module 14 is communicatively (electrically) connected to the image processing module 13 to receive the object detection image from the image processing module 13, and the display module 14 displays the object detection image labelled with the positions and names of the plurality of anatomical structures by means of a display. In one embodiment, the object detection image is a video.

Figure 1A:
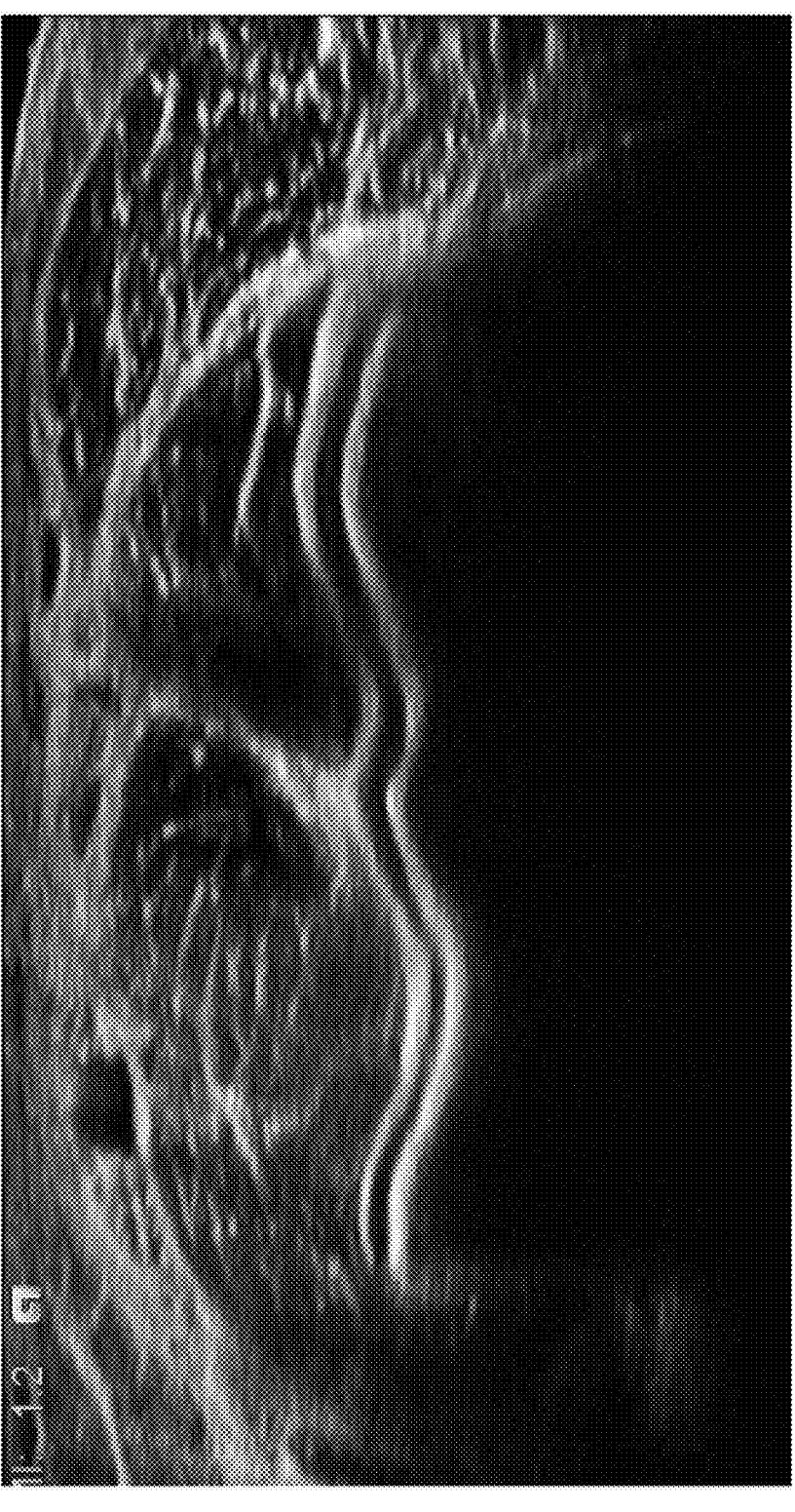
FIG. 1A is an ultrasound image showing the axial skeletal muscles near the elbow joint.
Figure 1B:
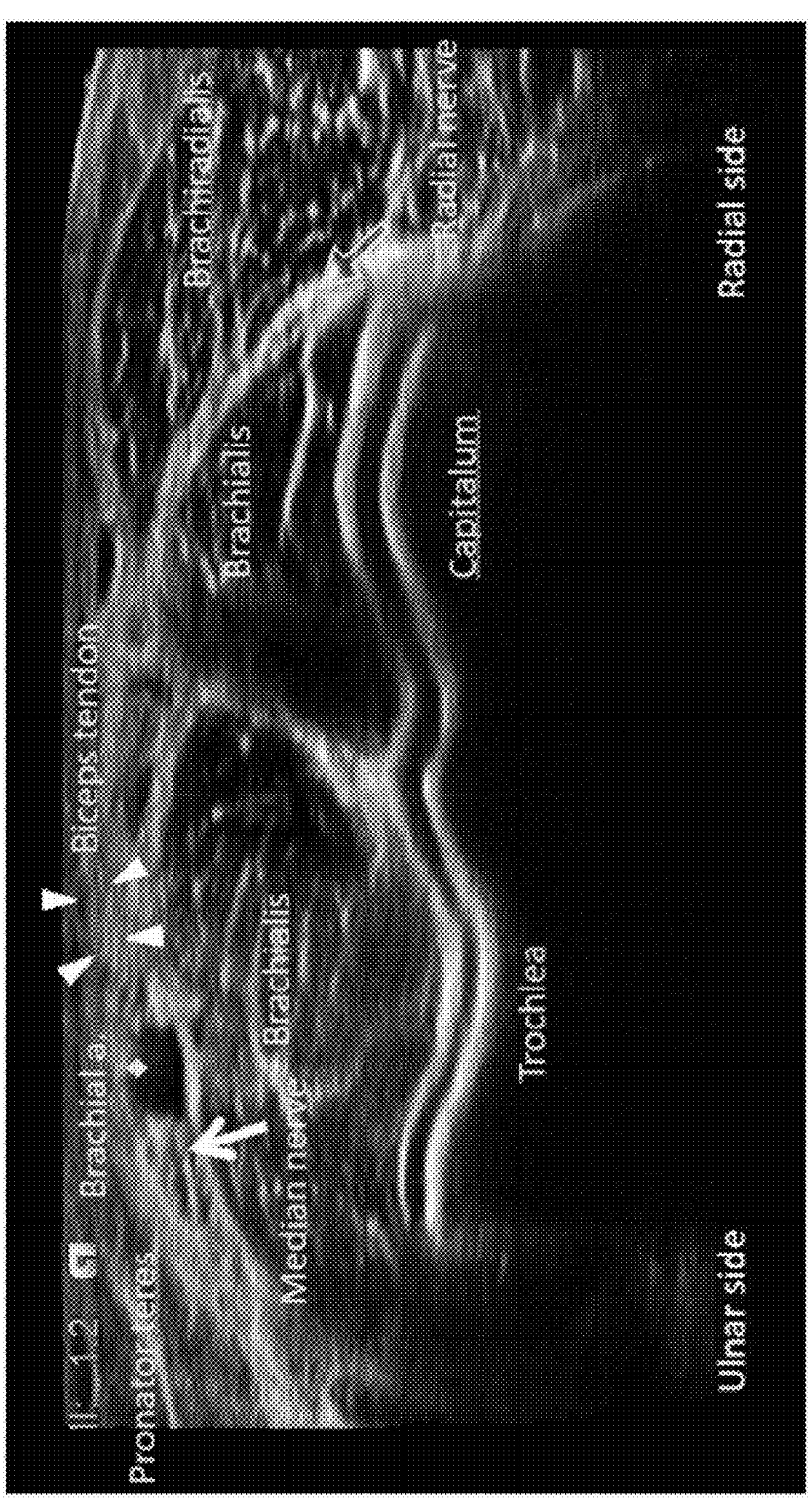
FIG. 1B is an ultrasound image showing the axial skeletal muscles near the labeled elbow joint.
Figure 2A:
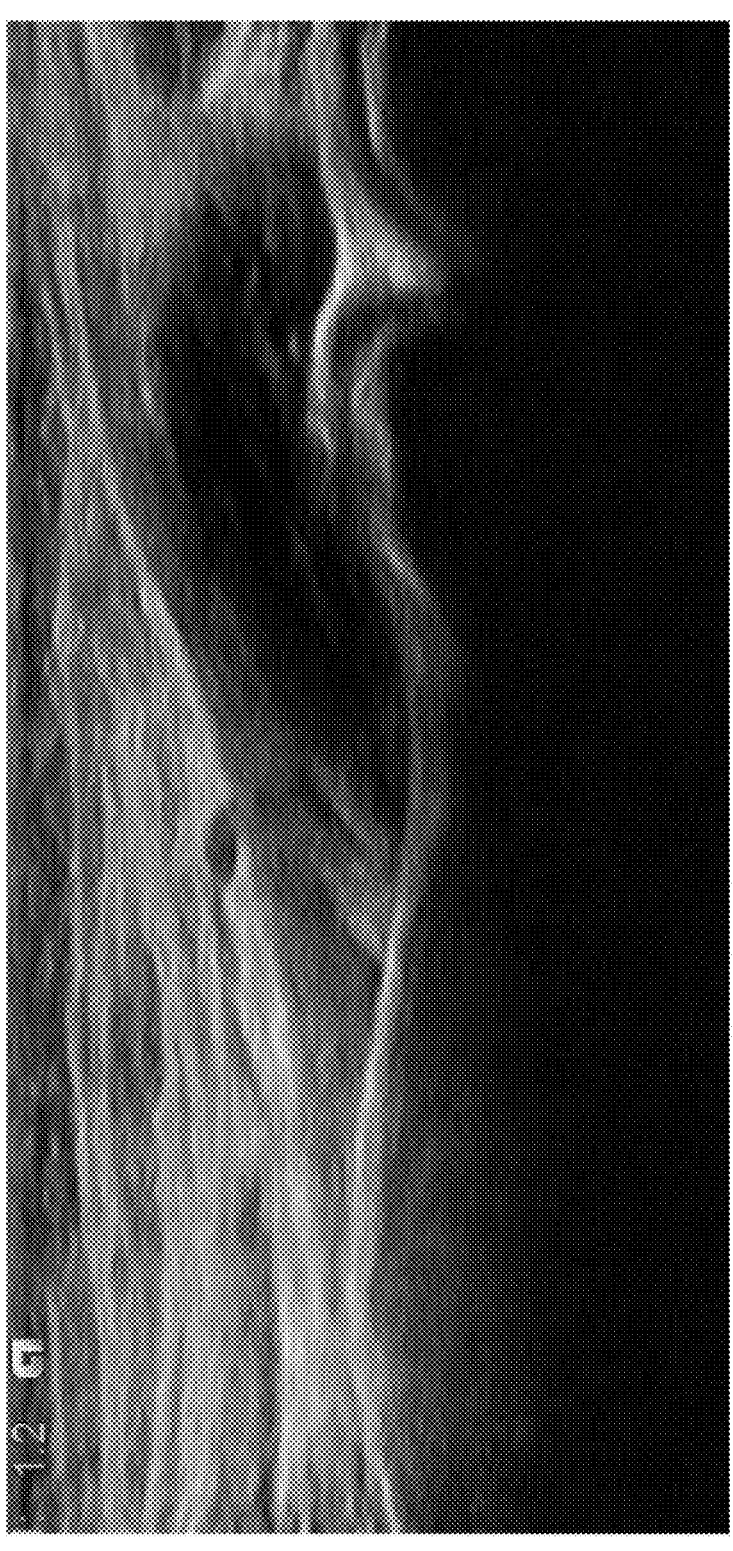
FIG. 2A is an ultrasound image showing the longitudinal unlabeled elbow joint after a 90-degree rotation.
Figure 2B:
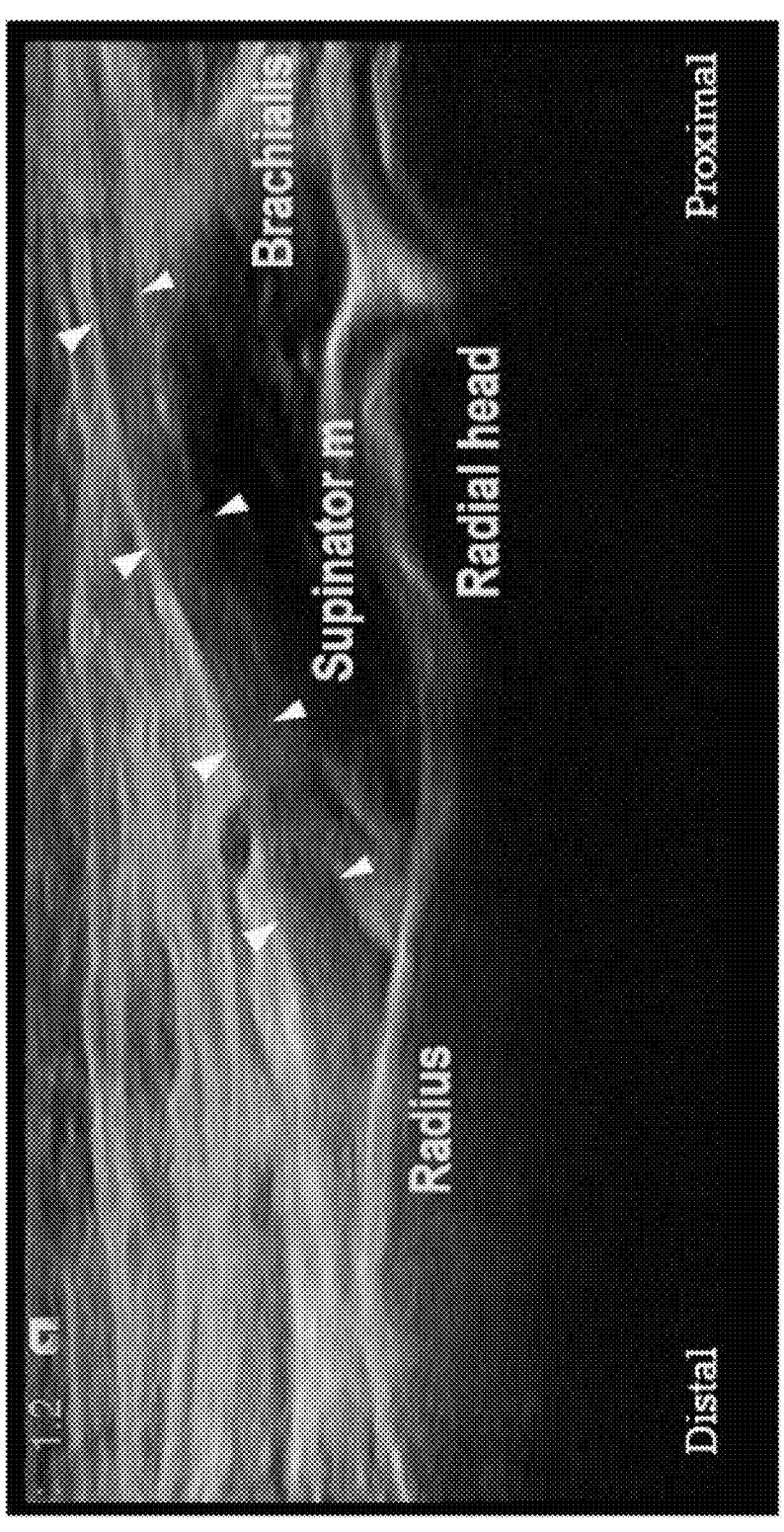
FIG. 2B is an ultrasound image showing the longitudinal labeled elbow joint after a 90-degree rotation.

FIG. 11 is a schematic flowchart showing an ultrasound image detection method based on AI automatic labeling of an anatomical structure according to the present disclosure, which is illustrated with reference to FIG. 1. In addition, the similarities between this embodiment and the aforesaid embodiment will not be repeated, and the method flow includes the following steps S111 to S114.

In step S111, the receiving module 11 in the ultrasound image detection system 1 based on AI automatic labeling of an anatomical structure receives an image to be recognized of an ultrasound apparatus 9.

In step S112, an image recognition module 12 uses the object detection model 12a thereof to detect objects of the plurality of anatomical structures in the image to be recognized, and automatically label the positions and names of the plurality of anatomical structures in the image to be recognized so as to obtain a continuous plurality of object recognition images with object detection results.

In step S113, an image processing module 13 sequentially receives the plurality of object recognition images from the image recognition module 12 to recalculate the confidence index of the anatomical structure in the plurality of object recognition images based on the object detection results of the plurality of object recognition images and to detect missed anatomical structures, thereby outputting an object detection image.

In step S114, a display module 14 displays the object detection image labeled with the positions and names of the plurality of anatomical structures for a user to watch by means of a display (e.g., a screen).

The following is a specific embodiment of the receiving module 11 in the ultrasound image detection system 1 based on AI automatic labeling of an anatomical structure according to the present disclosure. Similarly, the parts of this embodiment that are the same as those of the aforesaid embodiment will not be repeated herein.

In this embodiment, a physician scans a patient's arm with an ultrasound scanner (i.e., the ultrasound apparatus 9), and the ultrasound scanner transmits the image to be recognized scanned to the patient's arm to a receiving module 11, such that the image to be recognized is provided by the receiving module 11 to an image recognition module 12 having an object detection model 12a. Subsequently, the image recognition module 12 uses the object detection model 12a based on the convolution neural network to perform object detection on the image to be recognized so as to obtain a continuous plurality of object recognition images with object detection results.

Moreover, an image processing module 13 sequentially receives the plurality of object recognition images from the image recognition module 12, and uses at least one of the plurality of object recognition images received first as a reference image. Then, the other one of the plurality of object recognition images received later is used as an image to be recognized, such that a new confidence index of the plurality of anatomical structures in the image to be recognized is computed by the image processing module 13 according to a decay coefficient and object detection results of the image to be recognized and the reference image, so that the missed anatomical structure in the image to be recognized is labeled, thereby relabeling the missed anatomical structure in the plurality of object recognition images and outputting an object detection image.

Figure 12:
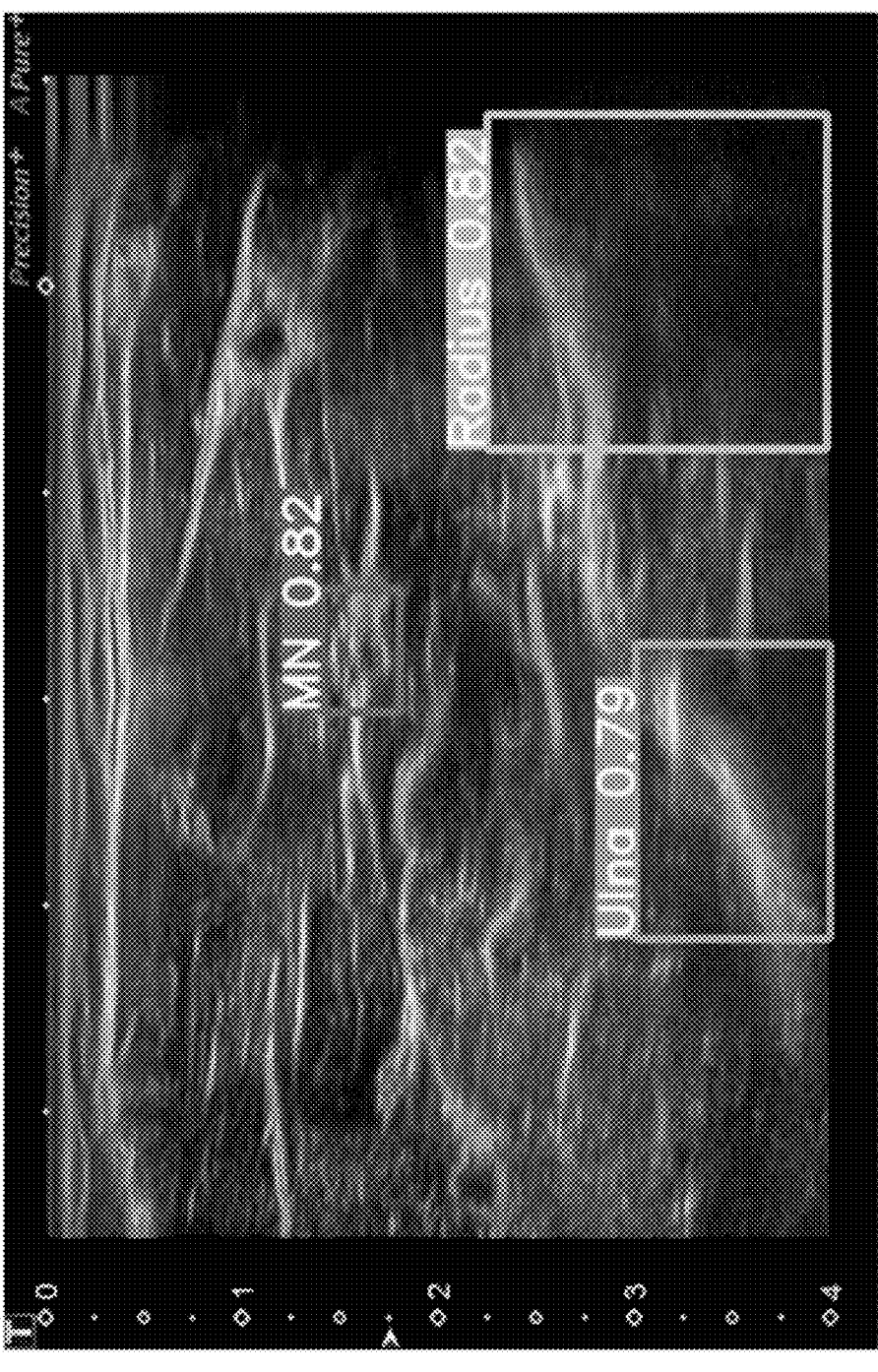
FIG. 12 is a schematic diagram showing an object detection image according to the present disclosure.

Finally, as shown in FIG. 12, a display module 14 displays the object detection image labeled with the positions and names of the plurality of anatomical structures to the physician by means of a screen for viewing, such that when the physician scans the patient's arm by the ultrasound scanner, the physician can simultaneously know the anatomical structures of the patient's arm scanned on the ultrasound image and the confidence index thereof (e.g., ulna: 0.79, radius: 0.82 and median nerve (MN): 0.82).

To sum up, the ultrasound image detection system and method thereof based on AI automatic labeling of an anatomical structure according to the present disclosure mainly detect each anatomical structure in an ultrasound image by an object detection model to label the position and name of each anatomical structure, thereby obtaining a plurality of object recognition images, and further compute a new confidence index of the anatomical structure by the object detection results of the plurality of object recognition images to label the missed anatomical structures in the plurality of object recognition images, thereby increasing accuracy of system inference; that is, the recognition accuracy of each anatomical structure in the plurality of object recognition images is improved.

In addition, the ultrasound image detection system and method thereof base on AI automatic labeling of an anatomical structure according to the present disclosure have the following advantages or technical effects.

I. The present disclosure uses the object detection model trained by deep learning to automatically and instantly recognize the anatomical structures on the ultrasound image by means of AI, and automatically add annotations, thereby assisting a physician to confirm the biological structures and names thereof in different scanning positions and directions.

II. The present disclosure uses a semi-supervised learning method to achieve the effect of automatically labeling training images by training teacher models and student models, and greatly reduces labor costs.

III. The present disclosure weights a current object recognition image (an image to be recognized) with reference to the object detection results of the previous several object recognition images (reference images) so as to obtain a weighted new result (a new confidence index) thereof. Therefore, the present disclosure utilizes the feature of the image continuity in the film, and improves each image that was originally recognized independently such that the results of the previous few images are referred to before being output during recognition. Consequently, even if the model does not have high confidence in the recognition of several images in a video and the tissue is not recognized, it can also recognize the less certain recognition results of the original neural network by referring to the results of the previous few images so as to improve accuracy of system recognition.

The foregoing embodiments are provided for the purpose of illustrating the principles and effects of the present disclosure, rather than limiting the present disclosure. Anyone skilled in the art can modify and alter the above embodiments without departing from the spirit and scope of the present disclosure. Therefore, the scope of protection with regard to the present disclosure should be as defined in the accompanying claims listed below.

What is claimed is:

1. An ultrasound image detection system based on artificial intelligence automatic labeling of an anatomical structure, the ultrasound image detection system comprising:

a receiving module, executed by a processor, configured to receive an image to be recognized from an ultrasound apparatus;

an image recognition module, executed by the processor, having an object detection model and communicatively connected to the receiving module to receive the image to be recognized, such that the object detection model is used to detect a plurality of anatomical structures in the image to be recognized, thereby obtaining a plurality of object recognition images with object detection results;

an image processing module, executed by the processor, communicatively connected to the image recognition module to receive the plurality of object recognition images, wherein the image processing module uses at least one of the plurality of object recognition images received first as at least one reference image and the other one of the plurality of object recognition images received subsequently as an image to be recognized, such that a new confidence index of the plurality of anatomical structures in the image to be recognized is computed according to the object detection results of the image to be recognized and the reference image, a decay coefficient and a distance between the reference image and the image to be recognized so as to label missed anatomical structures in the image to be recognized, thereby detecting the missed anatomical structures and outputting an object detection image; and a display module, executed by the processor, communicatively connected to the image processing module to receive the object detection image and display the object detection image in real time.

2. The ultrasound image detection system of claim 1, further comprising an automatic labeling module, executed by the processor, communicatively connected to the image recognition module and configured to use a semi-supervised learning to train a teacher model and a student model, such that the automatic labeling module uses the trained teacher model to label unlabeled plural ultrasound images to generate a plurality of training images, thereby providing for the image recognition module to train the object detection model.

3. The ultrasound image detection system of claim 1, wherein the object detection model includes a Focus framework which performs a slicing operation on the received image to be recognized, such that a feature map of the image to be recognized is obtained, thereby providing for the object detection model to detect a plurality of anatomical structures in the image to be recognized.

4. The ultrasound image detection system of claim 1, wherein the object detection image includes positions and names of the plurality of anatomical structures.

5. An ultrasound image detection method based on artificial intelligence automatic labeling of an anatomical structure, the ultrasound image detection method comprising:

receiving an image to be recognized from an ultrasound apparatus by a receiving module, executed by a processor;

receiving the image to be recognized from the receiving module by an image recognition module having an object detection model and executed by the processor, such that the image recognition module uses the object detection model to detect a plurality of anatomical structures in the image to be recognized, thereby obtaining a plurality of object recognition images with object detection results;

receiving the plurality of object recognition images from the image recognition module by an image processing module executed by the processor, and using at least one of the plurality of object recognition images received first as at least one reference image and the other one of the plurality of object recognition images received subsequently as an image to be recognized by the image processing module, such that the image processing module computes a new confidence index of the plurality of anatomical structures in the image to be recognized according to the object detection results of the image to be recognized and the reference image, a decay coefficient and a distance between the reference image and the image to be recognized so as to label missed anatomical structures in the image to be recognized, thereby detecting the missed anatomical structures and outputting an object detection image; and receiving the object detection image by a display module executed by the processor to display the object detection image in real time.

6. The ultrasound image detection method of claim 5, further comprising using a semi-supervised learning to train a teacher model and a student model by an automatic labeling module executed by the processor, such that the automatic labeling module uses the trained teacher model to label unlabeled plural ultrasound images to generate a plurality of training images, thereby providing for the image recognition module to train the object detection model.

7. The ultrasound image detection method of claim 5, further comprising using a Focus framework to perform a slicing operation on the received image to be recognized by the object detection model, such that a feature map of the image to be recognized is obtained, thereby providing for the object detection model to detect a plurality of anatomical structures in the image to be recognized.

8. The ultrasound image detection method of claim 5, wherein the object detection image includes positions and names of the plurality of anatomical structures.

* * * * *